(12) United States Patent
Kurochi et al.

(10) Patent No.: US 9,271,683 B2
(45) Date of Patent: Mar. 1, 2016

(54) RADIATION FOCAL POSITION DETECTING METHOD, RADIATION DETECTING APPARATUS AND RADIATION TOMOGRAPHIC IMAGING APPARATUS

(71) Applicant: General Electric Company, Schenectady, NY (US)

(72) Inventors: Haruo Kurochi, Tokyo (JP); Ikhlef Abdelaziz, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 376 days.

(21) Appl. No.: 13/690,616

(22) Filed: Nov. 30, 2012

(65) Prior Publication Data

US 2014/0153691 A1 Jun. 5, 2014

(51) Int. Cl.
*A61B 6/03* (2006.01)
*A61B 6/00* (2006.01)
*G06T 11/00* (2006.01)

(52) U.S. Cl.
CPC .............. *A61B 6/032* (2013.01); *A61B 6/4078* (2013.01); *A61B 6/4233* (2013.01); *A61B 6/4291* (2013.01); *A61B 6/5205* (2013.01); *A61B 6/58* (2013.01); *G06T 11/005* (2013.01)

(58) Field of Classification Search
CPC .......................................................... A61B 6/00
USPC ..................................................... 378/19, 207
See application file for complete search history.

(56) References Cited

U.S. PATENT DOCUMENTS

| | | | |
|---|---|---|---|
| 5,566,220 A * | 10/1996 | Saito et al. | 378/138 |
| 7,612,343 B2 | 11/2009 | Vickers | |
| 7,844,032 B2 | 11/2010 | Vermilyea et al. | |
| 7,916,839 B2 | 3/2011 | Halazonetis et al. | |
| 8,126,119 B2 | 2/2012 | Kurochi | |
| 8,139,717 B2 | 3/2012 | Harding et al. | |
| 2002/0080922 A1 * | 6/2002 | Kwasnick et al. | 378/205 |
| 2004/0264648 A1 * | 12/2004 | Claus et al. | 378/163 |
| 2005/0129175 A1 * | 6/2005 | Shen | A61B 6/032 378/62 |
| 2009/0225955 A1 | 9/2009 | Igarashi et al. | |
| 2011/0096895 A1 | 4/2011 | Kurochi | |
| 2011/0176663 A1 * | 7/2011 | Shaughnessy | 378/154 |
| 2013/0223588 A1 * | 8/2013 | Kurochi et al. | 378/19 |

FOREIGN PATENT DOCUMENTS

| | | | |
|---|---|---|---|
| JP | 06-169914 | 6/1994 | |
| JP | 08-280659 | 10/1996 | |
| JP | WO 2011036968 A1 * | 3/2011 | A61B 6/032 |

* cited by examiner

*Primary Examiner* — Phillip A Johnston
*Assistant Examiner* — Eliza Osenbaugh-Stewart
(74) *Attorney, Agent, or Firm* — Lucas Divine; General Electric Company

(57) ABSTRACT

A radiation focal position detecting method for detecting a positional displacement of a focal point of a radiation source in a radiation tomographic imaging apparatus is provided. The method includes providing a radiation absorber that covers parts of first and second detecting element regions, the parts lying on mutually adjoining sides of the first and second detecting element regions in a radiation detector including a plurality of detecting elements arranged in channel and slice directions, and specifying, based on intensities of radiation detected by the detecting elements in the first and second detecting element regions, a position of the focal point or an amount of movement of the focal point from a reference position.

22 Claims, 9 Drawing Sheets

RADIATION FOCAL POSITION DETECTING METHOD, RADIATION DETECTING APPARATUS AND RADIATION TOMOGRAPHIC IMAGING APPARATUS

BACKGROUND OF THE INVENTION

The present invention relates to a radiation focal position detecting method, a radiation detecting apparatus and a radiation tomographic imaging apparatus, and more specifically to a technology which detects a positional displacement of a radiation focal point of a radiation source in high resolution.

In a radiation tomographic imaging apparatus having a multi-detector, such as a multi-slice X-ray CT apparatus or the like, the accuracy of position of a radiation focal point of a radiation source is very important in maintaining an acquired image in high quality. A position error in the radiation focal point may affect the geometry of a data acquisition system, thus resulting in the occurrence of serious artifacts in a high resolution region of the acquired image. In a recent radiation detecting apparatus in particular, a two-dimensional collimator having collimator plates arranged in channel and slice directions are often used to reduce scattered radiation incident to each detecting element. In this case, the adverse effect due to the position error in the radiation focal point becomes more serious.

The movement of the radiation focal point due to a change in the temperature of the radiation source has heretofore been present as almost inevitable. As its countermeasures, the position of the radiation focal point and the amount of movement thereof are detected based on, for example, a reference channel of a radiation detector. That is, profiles of radiation detection signals in a reference detecting element group, and the correction of projection data and control on radiation in a radiation direction have been conducted based on the so-detected information. See, for example, Japanese Patent Laid-Open No. Hei 6-169914, FIGS. 8 through 13, etc., and Japanese Patent Laid-Open No. Hei 8-280659, FIG. 10, etc.

The detecting elements and the collimator plates have however been miniaturized in recent years, and the general related art method as described above has difficulty detecting the position of the radiation focal point and the amount of movement thereof with sufficient resolution.

With such circumstances, there has been a demand for a technology capable of detecting a positional displacement of the radiation focal point of the radiation source in high resolution.

BRIEF DESCRIPTION OF THE INVENTION

The systems and methods disclosed herein detect a positional displacement of a focal point of a radiation source in a radiation tomographic imaging apparatus in high resolution.

In a first aspect, a radiation focal position detecting method for detecting a positional displacement of a focal point of a radiation source in a radiation tomographic imaging apparatus is provided. The method includes providing a radiation absorber so as to cover parts of first and second detecting element regions, lying on mutually adjoining sides thereof in a radiation detector including a plurality of detecting elements arranged in channel and slice directions and specifying a position of the focal point or an amount of movement thereof from a reference position, based on the intensities of radiation detected by the detecting elements in the first and second detecting element regions.

In a second aspect, the radiation focal position detecting method according to the first aspect is provided, wherein the width of the radiation absorber in a direction of proximity of the first and second detecting element regions to each other is wider than the thickness of each of collimator plates for separating the detecting elements.

In a third aspect, the radiation focal position detecting method according to the first or second aspect is provided, wherein the first and second detecting element regions are adjacent to each other in the slice direction.

In a fourth aspect, the radiation focal position detecting method according to any one of the first through third aspects is provided, wherein the first and second detecting element regions are located in the neighborhood of ends in the channel direction of the detecting elements.

In a fifth aspect, the radiation focal position detecting method according to any one of the first through fourth aspects is provided, wherein the first and second detecting element regions are located in the neighborhood of a center in the slice direction of the detecting elements.

In a sixth aspect, the radiation focal position detecting method according to any one of the first through fifth aspects is provided, wherein the first and second detecting element regions are reference channels in the radiation detector.

In a seventh aspect, the radiation focal position detecting method according to any one of the first through sixth aspects is provided, wherein the first and second detecting element regions respectively include regions of two or more detecting elements.

In an eighth aspect, the radiation focal position detecting method according to any one of the first through sixth aspects is provided, wherein the first and second detecting element regions are adjacent to each other and respectively have a width of one detecting element in their adjacent directions, and wherein the radiation absorber has a width of 50% to 150% of the width of the one detecting element in the adjacent directions.

In a ninth aspect, the radiation focal position detecting method according to any one of the first through eighth aspects is provided, wherein the radiation absorber is provided at a position 10 mm to 100 mm away in a direction toward the radiation source from detection surfaces of the first and second detecting element regions.

In a tenth aspect, the radiation focal position detecting method according to any one of the first through ninth aspects is provided, wherein the position of a center of the radiation absorber in the direction of the proximity of the first and second detecting element regions to each other is an intermediate position between the first and second detecting element regions.

In an eleventh aspect, a radiation detecting apparatus is provided. The radiation detecting apparatus includes a radiation detector including a plurality of detecting elements arranged in channel and slice directions, and a radiation absorber provided so as to cover parts of first and second detecting element regions in the radiation detector, the parts lying on mutually adjoining sides of the first and second detecting element regions.

In a twelfth aspect, the radiation detecting apparatus according to the eleventh aspect is provided, wherein the width of the radiation absorber in a direction of proximity of the first and second detecting element regions to each other is wider than the thickness of each of collimator plates for separating the detecting elements.

In a thirteenth aspect, the radiation detecting apparatus according to the eleventh or twelfth aspect is provided, wherein the first and second detecting element regions are adjacent to each other in the slice direction.

In a fourteenth aspect, the radiation detecting apparatus according to any one of the eleventh through thirteenth aspects is provided, wherein the first and second detecting element regions are adjacent to each other and respectively have a width of one detecting element in their adjacent directions, and wherein the radiation absorber has a width of 50% to 150% of the width of the one detecting element in the adjacent directions.

In a fifteenth aspect, the radiation detecting apparatus according to any one of the eleventh through fourteenth aspects is provided, wherein the position of a center of the radiation absorber in the direction of the proximity of the first and second detecting element regions to each other is an intermediate position between the first and second detecting element regions.

In a sixteenth aspect, a radiation tomographic imaging apparatus is provided. The radiation tomographic imaging apparatus includes a radiation source, a radiation detector including a plurality of detecting elements arranged in channel and slice directions, a radiation absorber provided so as to cover parts of first and second detecting element regions in the radiation detector, the parts lying on mutually adjoining sides of the first and second detecting element regions, and a specifying device which specifies a position of a focal point of the radiation source or an amount of movement thereof from a reference position, based on the intensities of radiation emitted from the focal point of the radiation source and detected by the detecting elements in the first and second detecting element regions.

In a seventeenth aspect, the radiation tomographic imaging apparatus according to the sixteenth aspect is provided, wherein the width of the radiation absorber in a direction of proximity of the first and second detecting element regions to each other is wider than the thickness of each of collimator plates for separating the detecting elements.

In an eighteenth aspect, the radiation tomographic imaging apparatus according to the sixteenth or seventeenth aspect is provided, wherein the first and second detecting element regions are adjacent to each other in the slice direction.

In a nineteenth aspect, the radiation tomographic imaging apparatus according to any one of the sixteenth through eighteenth aspects is provided, wherein the first and second detecting element regions are adjacent to each other and respectively have a width of one detecting element in their adjacent directions, and wherein the radiation absorber has a width of 50% to 150% of the width of the one detecting element in the adjacent directions.

In a twentieth aspect, the radiation tomographic imaging apparatus according to any one of the sixteenth through nineteenth aspects is provided, wherein the position of a center of the radiation absorber in the direction of the proximity of the first and second detecting element regions to each other is an intermediate position between the first and second detecting element regions.

According to the above aspects, an X-ray absorber is provided so as to cover parts on the mutually adjoining sides of first and second detecting element regions. Therefore, the ratio between a region irradiated with radiation in the first detecting element region and a region irradiated with radiation in the second detecting element region is determined according to the position of a radiation focal point of a radiation source. When the radiation focal point is moved, the ratio therebetween changes greatly. Thus, a positional displacement of the radiation focal point can be detected in high resolution based on the intensities of radiation detected by the first and second detecting element regions.

Further advantages will be apparent from the following description of exemplary embodiments as illustrated in the accompanying drawings.

DETAILED DESCRIPTION OF THE INVENTION

Exemplary embodiments will hereinafter be described. Incidentally, the disclosure is not limited to or by the embodiments specifically described herein.

First Embodiment

Figure 1:
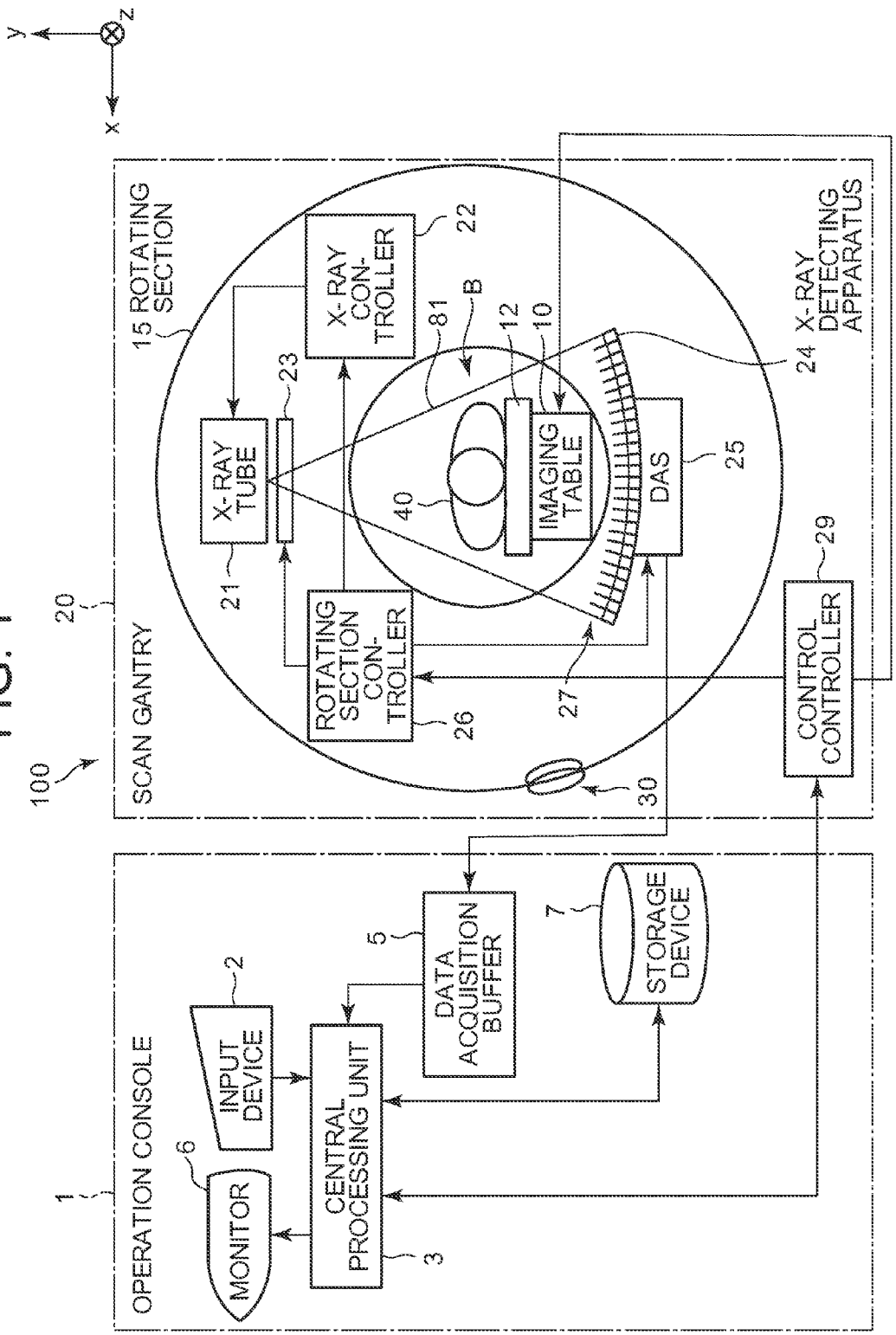
FIG. 1 is a diagram schematically showing a configuration of an X-ray CT apparatus according to an exemplary embodiment.

FIG. 1 is a diagram schematically showing a configuration of an X-ray CT apparatus according to a first embodiment.

The X-ray CT apparatus 100 is equipped with an operation console 1, an imaging table 10 and a scan gantry 20.

The operation console 1 is equipped with an input device 2 which accepts an input from an operator, a central processing unit 3 which performs control of respective parts for performing subject's imaging, a data process for generating an image, etc., a data acquisition buffer 5 which acquires or collects data acquired by the scan gantry 20, a monitor 6 which displays each image thereon, and a storage device 7 which stores programs, data, etc. therein.

The imaging table 10 is equipped with a cradle 12 which inserts and draws a subject 40 into and from an opening B of the scan gantry 20 with the subject 40 placed thereon. The cradle 12 is elevated and linearly moved horizontally by a motor built in the imaging table 10. Incidentally, in the present embodiment, the direction of a body axis of the subject 40, i.e., the horizontal linear moving direction of the cradle 12 is assumed to be a z direction, its vertical direction is assumed to be a y direction, and its horizontal direction orthogonal to the z and y directions is assumed to be an x direction.

The scan gantry 20 has an annular-shaped rotating section 15 supported rotatably about the opening B. The rotating section 15 is provided with an X-ray tube 21, an X-ray controller 22 which controls the X-ray tube 21, an aperture 23 which shapes X-rays 81 generated from the X-ray tube 21 into a fan beam or a cone beam, an X-ray detecting apparatus 24 which detects the X-rays 81 penetrated through the subject 40, a DAS (Data Acquisition System) 25 which converts outputs of the X-ray detecting apparatus 24 into X-ray projection data and acquires or collects the same, and a rotating section controller 26 which controls the X-ray controller 22, aperture 23 and DAS 25. The scan gantry 20 is equipped with a control controller 29 which performs communication of control signals or the like with the operation console 1 and the imaging table 10. The rotating section 15 is electrically coupled to a part supporting it via a slip ring 30. Incidentally, the DAS is also called a data acquisition system.

The X-ray tube 21 and the X-ray detecting apparatus 24 are disposed opposite to each other with an imaging space in which the subject 40 is placed, (i.e., the opening B of the scan gantry 20) interposed therebetween. When the rotating section 15 is rotated, the X-ray tube 21 and the X-ray detecting apparatus 24 are rotated about the subject 40 while their positional relation is maintained. The X-rays 81 of the fan beam or cone beam, which are radiated from the X-ray tube 21 and shaped by the aperture 23, penetrate the subject 40 and are applied onto a detection surface of the X-ray detecting apparatus 24. The direction of expansion of the X-rays 18 of the fan beam or cone beam at an xy plane is called a channel direction (CH direction), and the direction of expansion thereof in the z direction or the z direction itself is called a slice direction (SL direction).

A configuration of the X-ray detecting apparatus 24 will now be explained in detail.

Figure 2A:
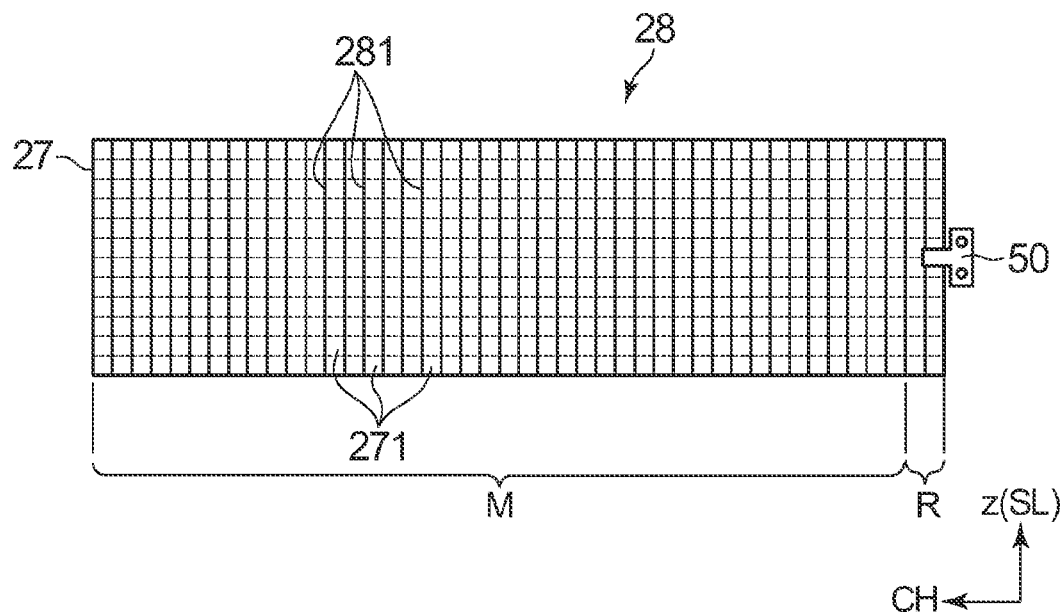
FIGS. 2A and 2B are diagrams illustrating a configuration example of an X-ray detecting apparatus.
Figure 2B:
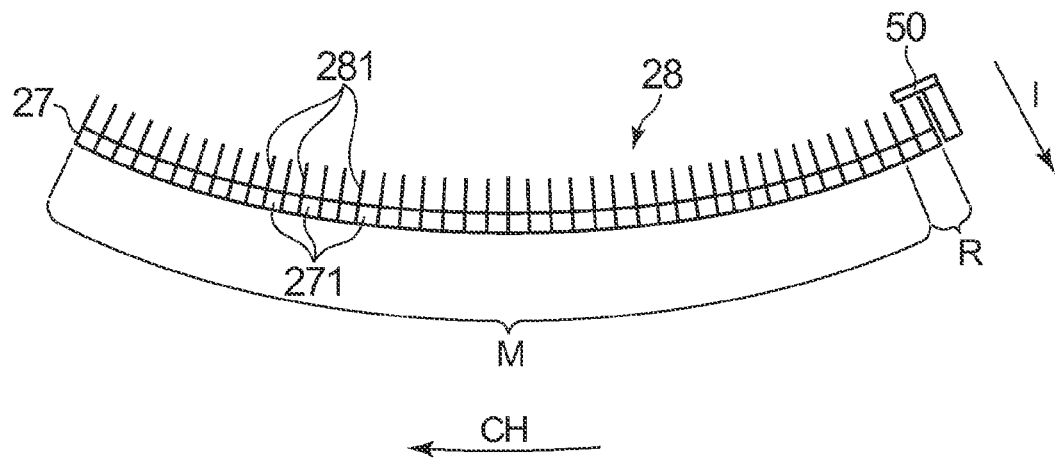

A configuration example of the X-ray detecting apparatus is shown in FIGS. 2A and 2B. FIG. 2A is a diagram (front diagram) as viewed from the X-ray tube 21 side, and FIG. 2B is a diagram (side diagram) as viewed in the z direction.

As shown in FIGS. 2A and 2B, the X-ray detecting apparatus 24 has an X-ray detector 27 and a collimator device 28.

The X-ray detector 27 has a configuration in which detecting elements 271 are arranged in matrix form in the CH and SL directions. The respective detecting elements 271 are placed along a slope curved surface in such a manner that their detection surfaces face an X-ray focal point 21$f$ of the X-ray tube 21. In the present embodiment, the detecting elements 271 in the X-ray detector 27 are arranged in, for example, 1000 channels×128 columns. The detection surface of each detecting element 271 is approximately square having a width of about 1.025 millimeters (mm). Incidentally, in FIGS. 2A and 2B, a smaller number of the detecting elements 271 are drawn for convenience.

The collimator device 28 is provided on the detection surface side of the X-ray detector 27. The collimator device 28 includes a plurality of collimator plates 281. The collimator plates 281 are provided in such a manner that the detecting elements 271 of the X-ray detector 27 are divided or separated in the CH direction. The collimator plates 281 are provided in such a manner that their plate surfaces extend parallel to a radiation direction of X-rays from the X-ray focal point 21$f$. The width in an I direction, of each collimator plate 281 is 20 mm or so, for example, and the thickness of each collimator plate 281 is 0.2 mm or so, for example.

As shown in FIGS. 2A and 2B, the X-ray detector 27 includes a main region M, and a reference region R. The reference region R is a region that is provided at at least one end in the CH direction, of the X-ray detector 27 and irradiated with X-rays which do not penetrate the subject 40. The main region M is a region other than the reference region R. Data detected by the detecting elements 271 in the main region M are used for image reconstruction. Data detected by the detecting elements 271 in the reference region R are used for the correction of the detected data in the main region M.

As shown in FIGS. 2A and 2B, in the present example, the collimator plates 281 are provided at the boundaries between the detecting elements 271 in such a manner as to separate the detecting elements 271 line by line in the CH direction.

As shown in FIGS. 2A and 2B as well, an X-ray absorber 50 is attached to an end of the X-ray detector 27 in the CH direction and a position in the neighborhood of its central part in the SL direction. The X-ray absorber 50 will be described below in detail.

Figure 3A:
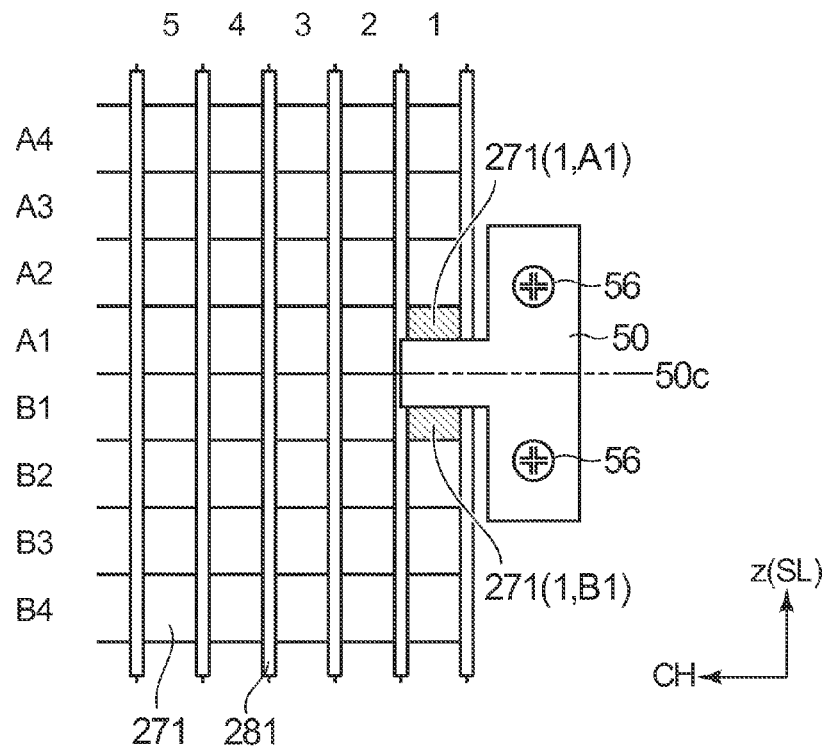
FIGS. 3A and 3B are partly enlarged diagrams (peripheral diagrams of X-ray absorber) of an X-ray detecting apparatus according to a first embodiment.
Figure 3B:
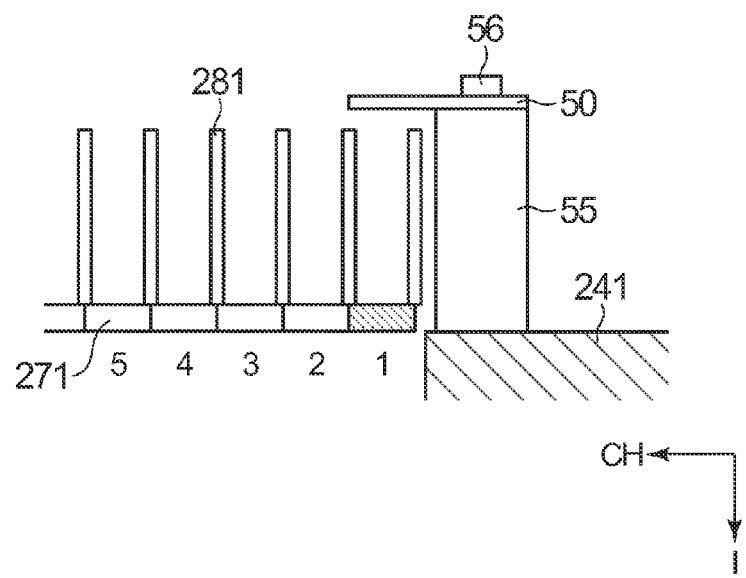

FIGS. 3A and 3B are partly enlarged diagrams of the X-ray detecting apparatus according to the first embodiment. FIG. 3A is a diagram (front diagram) taken when the periphery of the X-ray absorber 50 is seen from the X-ray tube 21 side, and FIG. 3B is diagram (side diagram) taken when the periphery of the X-ray absorber 50 is seen in the z direction.

Assume now that the individual detecting elements 271 that configure the X-ray detector 27 are respectively identified by channel and column numbers. The channel numbers are assumed to be 1, 2, . . . , 1000 from a −CH direction to a +CH direction in the X-ray detector 27. The column numbers are assumed to be A1, A2, . . . , A64 from the center of the X-ray detector 27 in the SL direction to the +z direction and B1, B2, . . . , B64 from the center thereof in the SL direction to the −z direction. Each detecting element 271 having a channel number i and a column number j is represented in the form of the detecting element 271 (i, j).

The detecting element 271 (1, A1) having the channel number 1 and the column number A1, and the detecting element 271 (1, B1) having the channel number 1 and the column number B1 are arranged adjacent to each other in the SL direction in the neighborhood of the SL-direction central part of the X-ray detector 27 at the end thereof in the −CH direction.

The X-ray absorber 50 is provided so as to shield X-rays applied to parts on the mutually adjoining sides in the SL direction, of a detection surface (detection surface of first detecting element region) of the detecting element 271 (1, A1) and a detection surface (detection surface of second detecting element region) of the detecting element 271 (1, B1), the X-rays being included in X-rays applied to the two detection surfaces. That is, the X-ray absorber 50 is disposed so as to cover portions adjacent to a boundary between the detection surface of the detecting element 271 (1, A1) and the detection surface of the detecting element 271 (1, B1) as viewed in the X-ray radiation direction (I direction). In the present example, the X-ray absorber 50 is mounted in such a manner that its central position 50$c$ in the SL direction is placed in an intermediate position, i.e., the boundary between the detection surfaces of the detecting elements 271 (1, A1) and 271 (1, B1).

The X-ray absorber 50 has a plate-like shape with the X-ray radiation direction as a plate thickness direction. An X-ray shielding portion thereof has a shape approximately rectangular as viewed in the X-ray radiation direction (I direction). The width of the X-ray absorber 50 in the SL direction is larger than the thickness of the collimator plate 281, e.g., it is equivalent to 50% to 150% of the width of one detecting element. In the present example, the width thereof is about 90% of the width of one detecting element. The thickness of the X-ray absorber 50 ranges from 0.1 mm to 1 mm, for example. In the present example, the thickness thereof is 0.2 mm or so. The position of the X-ray absorber 50 in the X-ray radiation direction (I direction) is located in, for example, a vertical position 10 mm to 100 mm away from the detection surface of the detecting element 271 to the X-ray focal point 21f of the X-ray tube 21, in the present example, a vertical position of 30 mm or so. An outer end in the CH direction of the X-ray absorber 50 is fastened and fixed with screws 56 through a spacer 55 or the like. Thus, when the X-ray focal point 21f is at a proper reference position z0 in design, approximately half of the detection surfaces of these detecting elements 271 are brought to a state of being shielded against the radiated X-rays 81. Incidentally, the X-ray absorber 50 is comprised of a heavy metal such as tungsten, molybdenum or the like.

A method of detecting the movement of the X-ray focal point and correcting X-ray projection data will now be described.

Figure 4:
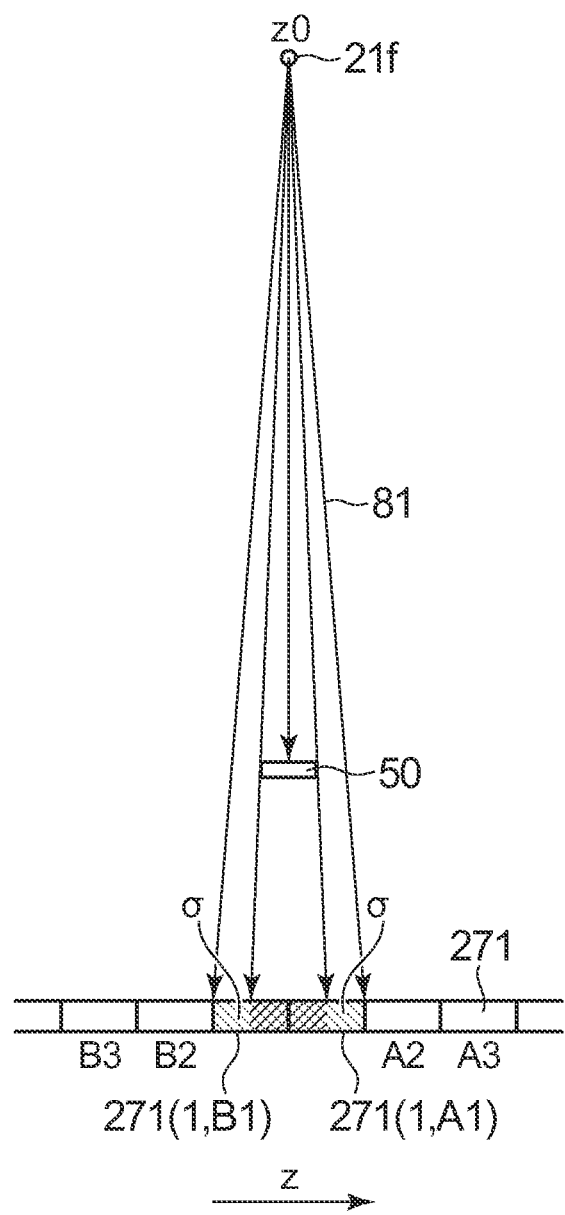
FIG. 4 is a diagram showing the manner of shielding against X-rays by the X-ray absorber when an X-ray focal point is placed in a reference position.
Figure 5:
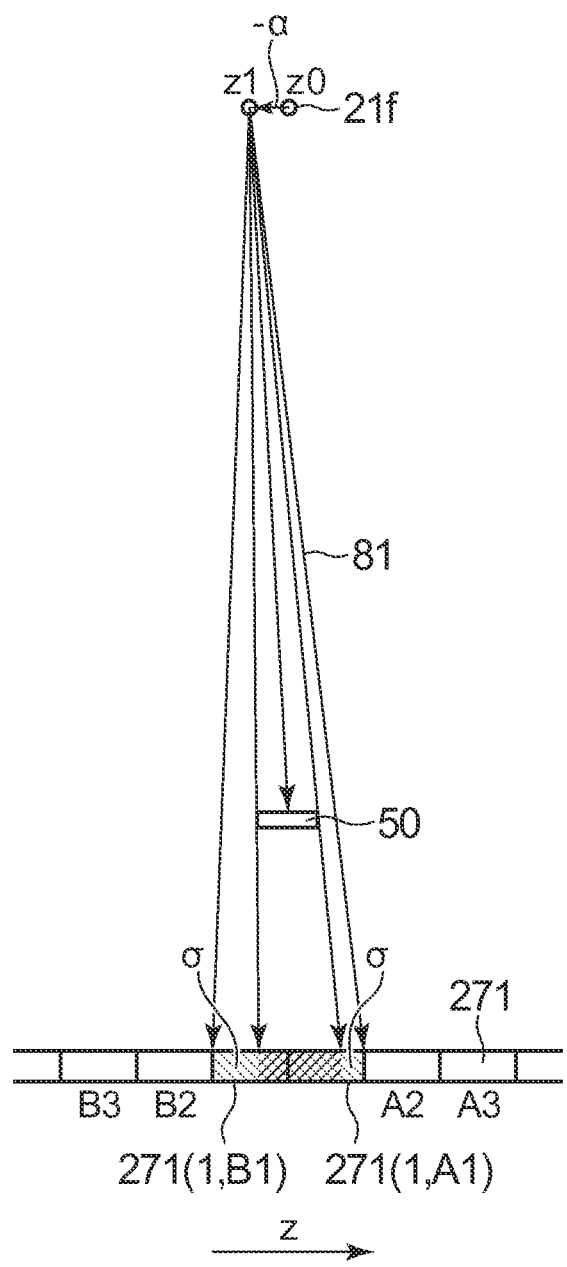
FIG. 5 is a diagram illustrating the manner of shielding against X-rays by the X-ray absorber when the X-ray focal point is moved in a −z direction from the reference position.
Figure 6:
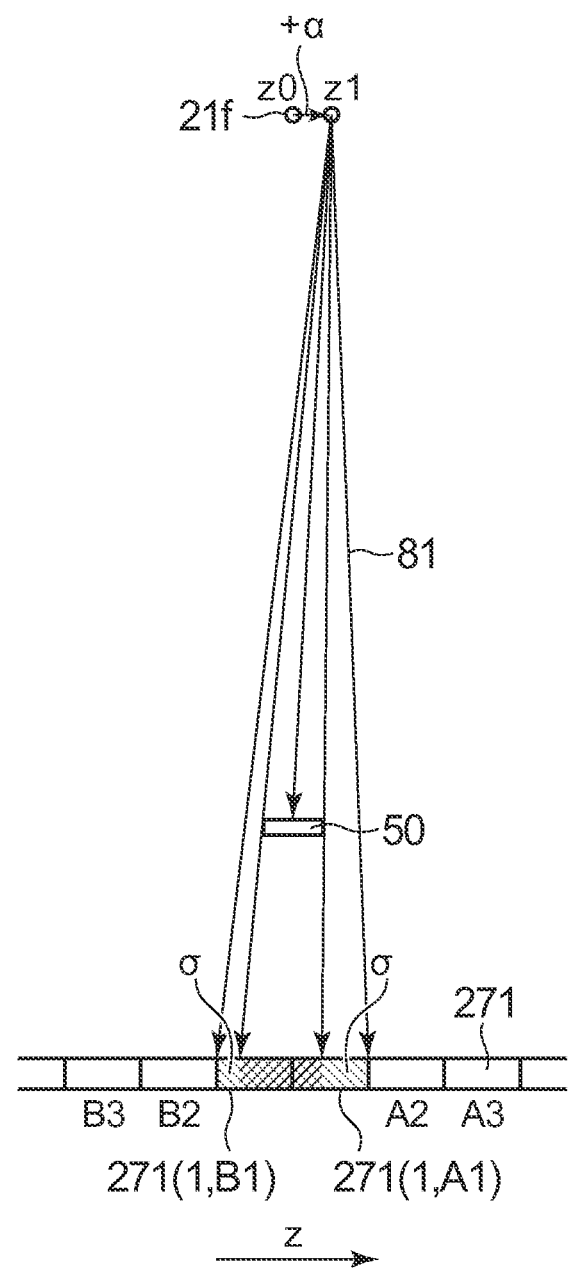
FIG. 6 is a diagram depicting the manner of shielding against X-rays by the X-ray absorber when the X-ray focal point is moved in a +z direction from the reference position.

FIGS. 4 through 6 are diagrams each showing the manner of X-ray shielding different depending on the position of the X-ray focal point.

Now consider that the position of the X-ray focal point 21f is shifted in the z direction, and the detection surfaces of the detecting elements 271 (1, A1) and 271 (1, B1) are irradiated with X-rays.

First, consider where when the X-ray focal point 21f is at the reference position z0 as shown in FIG. 4, i.e., when a z-direction position error ZE=0, X-rays are radiated from the X-ray focal point. In this case, a region (hereinafter called an X-ray radiation region) σ irradiated with the X-rays in the detection surface of the detecting element 271 (1, A1), and an X-ray radiation region σ of the detecting element 271 (1, B1) are approximately equal to each other.

Next, consider where when the X-ray focal point 21f is placed in a position z1 moved in the −z direction from the reference position z0 as shown in FIG. 5, i.e., when the z-direction position error $ZE=-\alpha(\alpha>0)$, X-rays 81 are applied from the X-ray focal point 21. In this case, when it is compared with when the X-ray focal point 21f is at the reference position z0, the X-ray radiation region σ of the detecting element 271 (1, A1) decreases and the X-ray radiation region σ of the detecting element 271 (1, B1) increases. That is, the X-ray radiation region σ of the detecting element 271 (1, A1) becomes smaller than the X-ray radiation region σ of the detecting element 271 (1, B1). As the amount α of movement of the focal point in the −z direction from the reference position z0 becomes larger, the X-ray radiation region σ of the detecting element 271 (1, A1) decreases and the X-ray radiation region σ of the detecting element 271 (1, B1) increases.

On the other hand, consider where when the X-ray focal point 21f is at a position z2 moved in the +z direction from the reference position z0 as shown in FIG. 6, i.e., when the z-direction position error $ZE=+\alpha(\alpha>0)$, X-rays 81 are radiated from the X-ray focal point 21f. In this case, when it is compared with when the X-ray focal point 21f is at the reference position z0, the X-ray radiation region σ of the detecting element 271 (1, A1) increases and the X-ray radiation region σ of the detecting element 271 (1, B1) decreases. That is, the X-ray radiation region σ of the detecting element 271 (1, A1) becomes larger than the X-ray radiation region σ of the detecting element 271 (1, B1). As the amount α of movement of the focal point in the +z direction from the reference position z0 becomes larger, the X-ray radiation region σ of the detecting element 271 (1, A1) increases and the X-ray radiation region σ of the detecting element 271 (1, B1) decreases.

Figure 7:
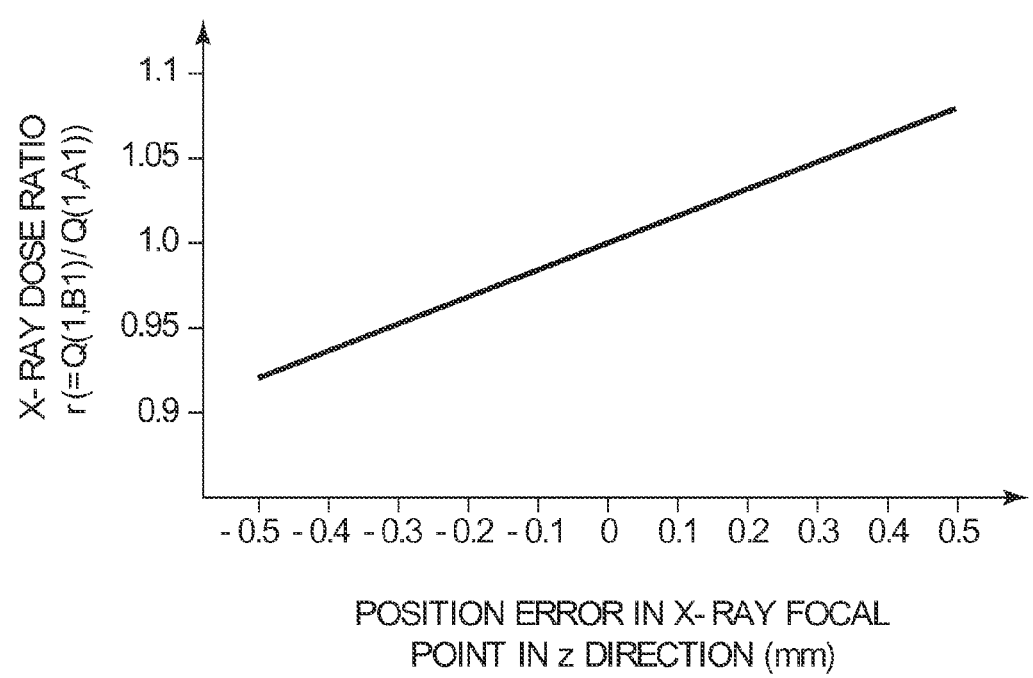
FIG. 7 is a graph showing the relationship between the ratio between X-ray doses received at two detecting elements whose detection surfaces are partly shielded by the X-ray absorber, and the position of an X-ray focal point.

Actually plotting the ratio Q (1, B1)/Q (1, A1) between X-ray doses received at the respective detection surfaces of the detecting element 271 (1, A1) and the detecting element 271 (1, B1) every Z-direction position error ZE yields such a graph as shown in FIG. 7, for example. As is understood from this graph, a variation in position (variation in X-ray radiation angle) of the X-ray focal point 21f is reflected on the X-ray doses Q (1, A1) and Q (1, B1) of the X-rays 81 received at the detection surfaces of the detecting element 271 (1, A1) and the detecting element 271 (1, B1). Accordingly, the balance between the X-ray doses Q (1, A1) and Q (1, B1) of the X-rays 81 received at the detection surfaces of the detecting element 271 (1, A1) and the detecting element 271 (1, B1) (e.g., the ratio r of the X-ray dose Q (1, B1) of the X-rays 81 received at the detection surface of the detecting element 271 (1, B1) to the X-ray dose Q (1, A1) of the X-rays 81 received at the detection surface of the detecting element 271 (1, A1)) becomes a monotone increasing function as shown in FIG. 7, and hence the X-ray dose ratio r and the z-direction position error ZE correspond to each other in a one-to-one relationship.

A relationship between the X-ray dose ratio r and the z-direction position error ZE such as shown in FIG. 7 is acquired in advance as a function table T1 of the entire X-ray detector 27. Simultaneously with it, output responses to the z-direction position errors ZE are determined as an inherent table T2 (i, j) with respect to the individual detecting elements 271 (i, j) of the X-ray detector 27. Even if the position of the X-ray focal point 21f varies upon imaging if done in this manner, the position thereof can be determined using the outputs of the detecting elements 271 (1, A1) and (1, B1) and the function table T1. By applying the determined position of X-ray focal point 21f to the table T2 (i, j), correction coefficients for all the detecting elements 271 can individually be provided in real time.

In the present example, changes in detection data corresponding to the z-direction position errors ZE are examined in advance every detecting element 271 (i, j) of the respective positions (i, j) in a main region M, based on the above principle. From the result of examination, a correction coefficient k for canceling the effects of the detection data due to the variation in the position of the X-ray focal point is determined as a function k (i, j, ZE) of the z-direction position error ZE and stored. The above function table T1 is also stored.

An X-ray dose ratio ry is determined from the outputs of the detecting elements 271 (1, A1) and (1, B1) for each acquired X-ray projection data Pv at each view v and applied to the function table T1, thereby determining the position of the X-ray focal point 21f corresponding to each view v. Detection data pv (i, j) obtained by each detecting element 271 (i, j), which configures X-ray projection data Pv of a view v to be processed, is corrected using the correction coefficient k (i, j, ZE).

Thus, a flow of processing in the X-ray CT apparatus according to the present embodiment will be explained.

Figure 8:
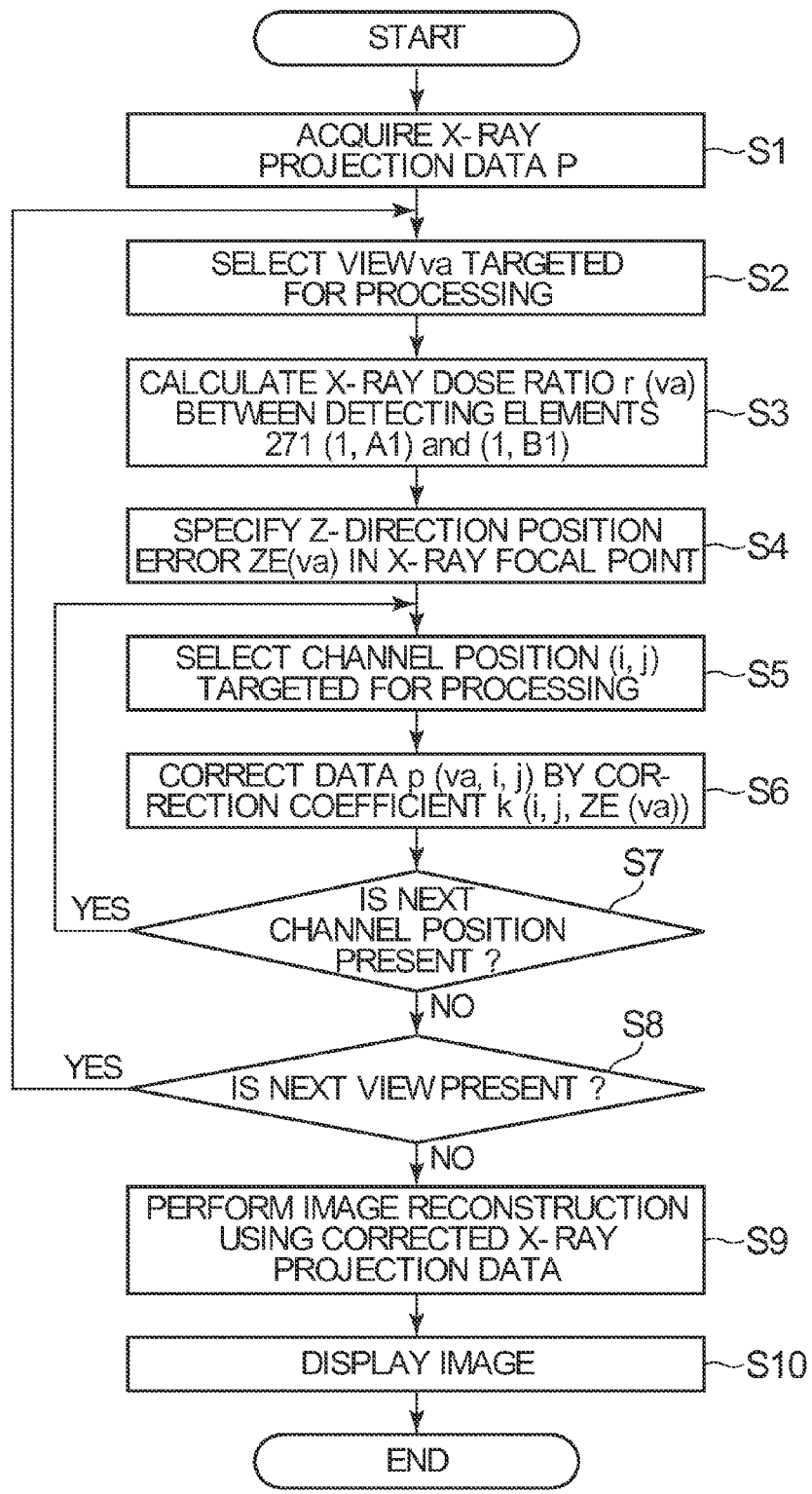
FIG. 8 is a flow diagram showing a flow of processing in the X-ray CT apparatus.

FIG. 8 is a flow diagram showing the flow of processing in the X-ray CT apparatus according to the present embodiment.

In Step S1, a subject is scanned to acquire X-ray projection data P of plural views v.

In Step S2, a view va of X-ray projection data targeted for processing is selected.

In Step S3, an X-ray dose ratio r is determined from detected signal values of the detecting elements 271 (1, A1) and 271 (1, B1) at the X-ray projection data P (va) of the selected view va.

In Step S4, the X-ray dose ratio r is applied to the function table T1 to determine a z-direction position error ZE (va) of an X-ray focal point corresponding to the view va.

In Step S5, a channel position (m, n) of detection data targeted for processing is selected.

In Step S6, detection data p (va, m, n) at the selected view va and channel position (m, n) is corrected using the correction coefficient k (m, n, ZE (va)).

In Step S7, it is determined whether a channel position to be next selected is present. When it is found to be present, the processing flow returns to Step S4, where a new channel position is selected. When it is found not to be present, the processing flow proceeds to the next Step S8.

In Step S8, it is determined whether a view to be next selected is present. When it is found to be present, the processing flow returns to Step S2, where a new view is selected. When it is found not to be present, the processing flow proceeds to the next Step S9.

In Step S9, image reconstruction is performed based on the corrected X-ray projection data of plural views.

In Step S10, a reconstructed image is displayed.

According to the present embodiment as described above, the X-ray absorber 50 is provided so as to cover the parts on the mutually adjoining sides, of the detection surfaces of the detecting elements 271 (1, A1) and (1, B1) in the SL direction, i.e., shield the radiated X-rays 81. Therefore, the ratio between the region σ irradiated with the X-rays 81 in the detection surface of the detecting element 271 (1, A1) and the region σ irradiated with the X-rays 81 in the detection surface of the detecting element 271 (1, B1) is fixed or determined according to the position of the X-ray focal point 21f. When the X-ray focal point 21f is moved, the ratio therebetween changes greatly. Thus, the position of the X-ray focal point 21f and the amount of movement thereof can be detected in high resolution, based on the X-ray intensities (detected signals) detected by these detecting elements.

Incidentally, when the width in the SL direction of the X-ray absorber 50 is about the thickness of the collimator plate 281, a significant difference is hard to occur between the X-ray dose Q of the X-rays detected by the detecting element 271 (1, A1) and the X-ray dose Q of the X-rays detected by the detecting element (1, B1) even if the X-ray focal point 21f is moved. That is, it is difficult to detect the position of the X-ray focal point 21f in high resolution. In the present embodiment, since the width of the X-ray absorber 50 is made wider than the thickness of the collimator plate 281, the change in the X-ray dose Q at each detection surface due to the movement of the X-ray foal point 21f can more positively be made large, and the movement of the X-ray focal point 21f can be detected with higher resolution.

Second Embodiment

Figure 9A:
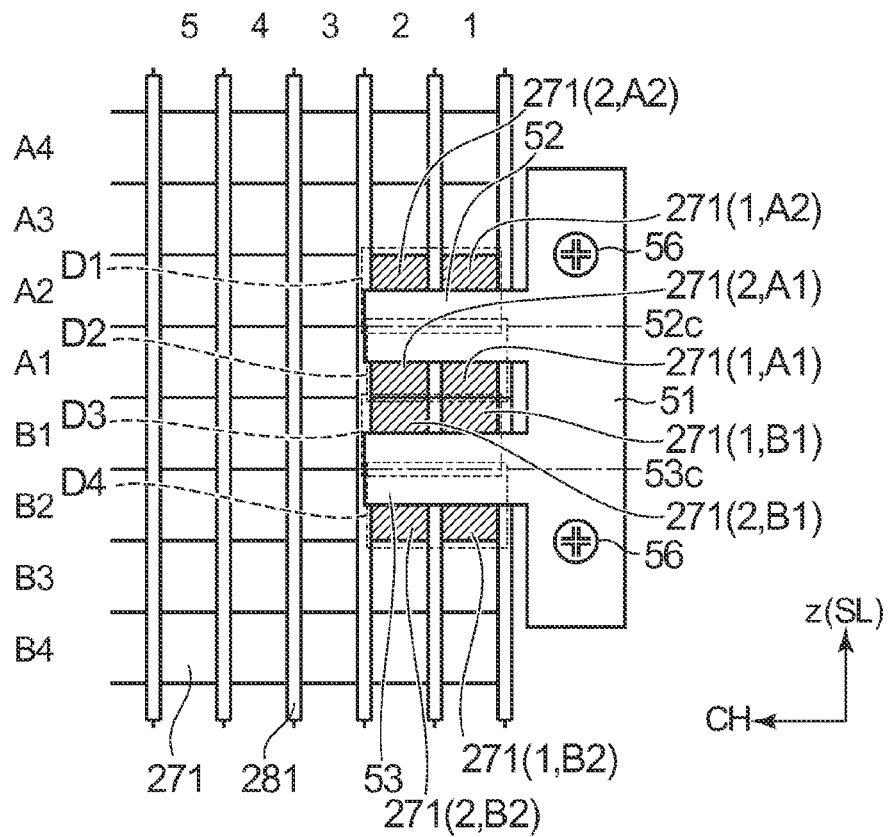
FIGS. 9A and 9B are partly enlarged diagrams (peripheral diagrams of X-ray absorber) of an X-ray detecting apparatus according to a second embodiment.
Figure 9B:
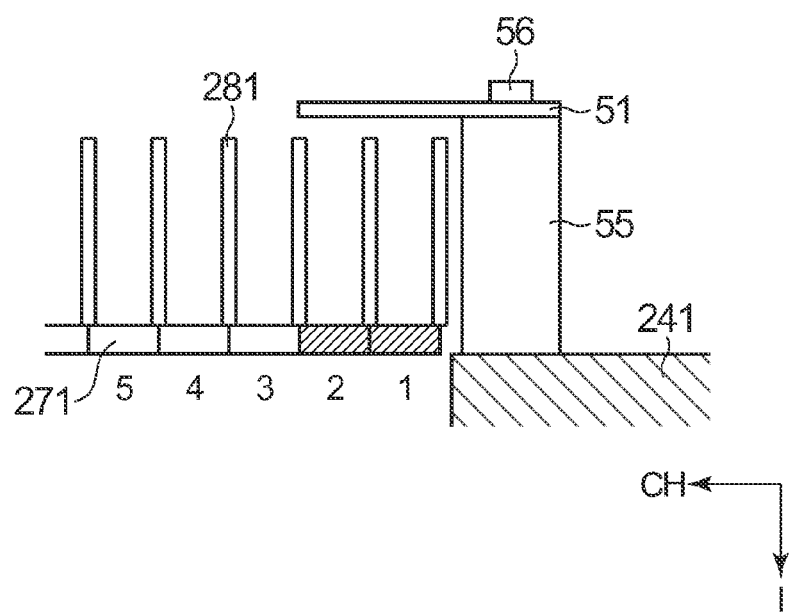

FIGS. 9A and 9B are partly enlarged diagrams of an X-ray detecting apparatus according to a second embodiment. FIG. 9A is a diagram (front diagram) as viewed from the X-ray tube 21 side, and FIG. 9B is a diagram (side diagram) as viewed in a z direction.

Incidentally, here, as shown in FIGS. 9A and 9B, a detection surface of a detecting element 271 (1, A2) and a detection surface of a detecting element (2, A2) are merged with each other to take on a first detection surface D1 (detection surface of first detecting element region). A detection surface of a detecting element 271 (1, A1) and a detection surface of a detecting element 271 (2, A1) are merged with each other to assume a second detection surface D2 (detection surface of a second detecting element region). A detection surface of a detecting element 271 (1, B1) and a detection surface of a detecting element (2, B1) are merged with each other to take on a third detection surface D3 (detection surface of first detecting element region). A detection surface of a detecting element 271 (1, B2) and a detection surface of a detecting element 271 (2, B2) are merged with each other to take on a fourth detection surface D4 (detection surface of second detecting element region).

As shown in FIGS. 9A and 9B, an X-ray absorber 51 in the present embodiment has a first X-ray absorption part 52 and a second X-ray absorption part 53. The first X-ray absorption part 52 shields X-rays 81 applied to parts of the first and second detection surfaces D1 and D2 lying on their mutually adjoining sides as viewed in an SL direction, the X-rays 81 being included in X-rays 81 applied to the first detection surface D1 and the second detection surface D2. That is, the first X-ray absorption part 52 is disposed so as to cover between the first detection surface D1 and the second detection surface D2. The second X-ray absorption part 53 shields X-rays 81 applied to parts of the third and fourth detection surfaces D3 and D4 lying on their mutually adjoining sides as viewed in the SL direction, the X-rays 81 being included in X-rays 81 applied to the third detection surface D3 and the fourth detection surface D4. That is, the second X-ray absorption part 53 is disposed so as to cover between the third detection surface D3 and the fourth detection surface D4. The first and second X-ray absorption parts 52 and 53 both have widths in the SL direction, which are about 90% of the width of one detecting element, and are approximately rectangular as viewed in an X-ray radiation direction (I direction).

In the present embodiment, the X-ray absorber 51 is formed and mounted in such a manner that the position 52c of the center of the first X-ray absorption part 52 in the SL direction is placed in an intermediate position between the first detection surface D1 and the second detection surface D2, and the position 53c of the center of the second X-ray absorption part 53 in the SL direction is placed in an intermediate position between the third detection surface D3 and the fourth detection surface D4. In the present embodiment, the first X-ray absorption part 52 and the second X-ray absorption part 53 are integrally formed. The X-ray absorber 51 is placed in a vertical position 30 mm away from these detection surfaces as viewed in the X-ray radiation direction (I direction).

From the above-described principle, even in such a configuration, the position of an X-ray focal point 21f can be detected and X-ray projection data p can be corrected, based on X-ray doses Q of the X-rays 81 detected at the first through fourth detection surfaces D1 through D4. The position of the X-ray focal point 21f can be detected and the X-ray projection data p can be corrected, for example, based on the ratio between the total X-ray dose Qt (or average X-ray dose Qa) of the X-rays 81 detected at the first detection surface D1 and the third detection surface D3, and the total X-ray dose Qt (or average X-ray dose Qa) of the X-rays 81 detected at the second detection surface D2 and the fourth detection surface D4. Also, for example, based on the ratio between the total X-ray dose Qt (or average X-ray dose Qa) of X-rays 81 detected at the first detection surface D1 and the total X-ray dose Qt (or average X-ray dose Qa) of X-rays 81 detected at the second detection surface D2, and the ratio between the total X-ray dose Qt (or average X-ray dose Qa) of X-rays 81 detected at the third detection surface D3 and the total X-ray dose Qt (or average X-ray dose Qa) of X-rays 81 detected at the fourth detection surface D4, the position of the X-ray focal point 21f can be detected and the X-ray projection data p can be corrected.

In the second embodiment, the first through fourth detection surfaces D1 through D4 respectively correspond to a plurality of detecting element regions, and the number of places therefor is also plural. It is therefore possible to reduce noise components included in data detected by the detecting elements 271 and reduce the effect due to variations in the accuracy of installation of the collimator plates 281. That is, it is possible to detect the position of the X-ray focal point 21f and correct the X-ray projection data p, based on characteristic amounts higher in SN ratio, thus resulting in improvements in their accuracy.

Incidentally, according to the above embodiments, since there are relatively few components to add as compared with the related art, there are relatively small increases in parts cost, and the degree of difficulty in production does not increase.

According to the above embodiments, since the effect due to the variations in the accuracy of installation of each collimator plate 281 is suppressed by virtue of the addition of such a correction algorithm as described above, the relaxation of specifications related to the accuracy of installation of each collimator plate 281 is enabled, and a so-called reduction in scrap cost can also be expected.

Incidentally, the disclosure is not limited to the above-described embodiments, but can be modified in various forms within the scope not departing from the gist of the present invention.

For example, in the above embodiments, the correlation between the X-ray dose ratio r between the detecting element regions, and the position of the X-ray focal point 21*f* is determined, the X-ray dose ratio r is determined from the actually-measured detected signal values, and the position of the X-ray focal point 21*f* is determined by reference to the correlation. The position of the X-ray focal point 21*f* may however of course be determined by another method. For example, there may be used a method for directly or indirectly determining the position of the X-ray focal point 21*f* from any characteristic value indicative of the balance between the detected signal values of the detecting elements (1, A1) and (1, B1).

Also, for example, in the above embodiments, the movement of the X-ray focal point 21*f* in the SL direction is detected based on the detected signal values of the detecting elements 271 adjacent to each other in the SL direction, and the variation in the X-ray projection data p due to the movement of the X-ray focal point is corrected. A configuration similar to this is however applied in the CH direction, whereby the movement of the X-ray focal point 21*f* in the CH direction can be detected and hence the variation in the X-ray projection data p due to the movement of the focal point can also be corrected. Alternatively, this configuration can also simultaneously be applied in the CH and SL directions.

Further, for example, in the above embodiments, the detection data of the specific detecting elements are acquired from the X-ray projection data p obtained by the actual scan of the subject 40, and the position of the X-ray focal point 21*f* is detected using these data. When a scan different from the actual scan, e.g., a scan for air-calibration prior to the actual scan, is performed, the detection data of the specific detecting elements are acquired and the position of the X-ray focal point 21*f* may be detected using the detection data. Since the X-ray focal point 21*f* often moves slowly in time in general, the correction of the X-ray projection data p is sufficiently enabled even if the timing provided to acquire the detection data used for correction, of each detecting element 271 and the timing provided to acquire the X-ray projection data p used for image reconstruction are slightly shifted from each other. The scan for the air-calibration also brings about an advantage that since no subject 40 is placed in the imaging space, it is possible to prevent detection data from being affected by scattered radiation.

For example, although each of the above embodiments is implemented in an X-ray CT apparatus, the systems and methods described herein are applicable even to a PET-CT apparatus or SPECT-CT apparatus in which the X-ray CT apparatus and PET or SPECT are combined together, etc.

What is claimed is:

1. A radiation focal position detecting method for detecting a positional displacement of a focal point of a radiation source in a radiation tomographic imaging apparatus, the method comprising: providing a single radiation absorber that has two absorption parts, each absorption part covering sections of two detecting element regions creating first, second, third, and fourth detecting element regions, the covered sections lying on mutually adjoining sides of the detecting element regions in a radiation detector including a plurality of detecting elements arranged in channel and slice directions; and specifying, based on intensities of radiation detected by the detecting elements in the first, second, third, and fourth detecting element regions, a position of the focal point or an amount of movement of the focal point from a reference position.

2. The radiation focal position detecting method according to claim 1, wherein a width of the radiation absorber in a direction of proximity of the first and second detecting element regions to each other is wider than a thickness of each of a plurality of collimator plates configured to separate the detecting elements.

3. The radiation focal position detecting method according to claim 1, wherein
   the first and second detecting element regions are adjacent to each other in the slice direction; and
   the third and fourth detecting element regions are adjacent to each other in the slice direction.

4. The radiation focal position detecting method according to claim 1, wherein the first and second detecting element regions are located in the neighborhood of ends in the channel direction of the detecting elements.

5. The radiation focal position detecting method according to claim 1, wherein the first and second detecting element regions are located in the neighborhood of a center in the slice direction of the detecting elements.

6. The radiation focal position detecting method according to claim 1, wherein the first and second detecting element regions are reference channels in the radiation detector, the reference channels configured to provide data used to correct image reconstruction data.

7. The radiation focal position detecting method according to claim 1, wherein the first and second detecting element regions each include regions of two or more detecting elements.

8. The radiation focal position detecting method according to claim 1, wherein the first and second detecting element regions are adjacent to each other and each have a width of one detecting element in their adjacent directions, and wherein the radiation absorber has a width of 50% to 150% of the width of the one detecting element in the adjacent directions.

9. The radiation focal position detecting method according to claim 1, wherein the radiation absorber is provided at a position at least 10 millimeters (mm) away in a direction toward the radiation source from detection surfaces of the first and second detecting element regions.

10. The radiation focal position detecting method according to claim 1, wherein a position of a center of the radiation absorber in a direction of proximity of the first and second detecting element regions to each other is an intermediate position between the first and second detecting element regions.

11. A radiation detecting apparatus comprising:
    a radiation detector including a plurality of detecting elements arranged in channel and slice directions;

a single radiation absorber with a plurality of absorption parts;

wherein a first absorption part covers first element parts of first and second detecting element regions in the radiation detector, said first element parts lying on mutually adjoining sides of the first and second detecting element regions; and wherein a second absorption part covers second element parts of third and fourth detecting element regions in the radiation detector, said second element parts lying on mutually adjoining sides of the third and fourth detecting element regions.

12. The radiation detecting apparatus according to claim 11, wherein a width of the radiation absorber in a direction of proximity of the first and second detecting element regions to each other is wider than a thickness of each of a plurality of collimator plates configured to separate the detecting elements.

13. The radiation detecting apparatus according to claim 11, wherein
the first and second detecting element regions are adjacent to each other in the slice direction; and
the third and fourth detecting element regions are adjacent to each other in the slice direction.

14. The radiation detecting apparatus according to claim 11,
wherein the first and second detecting element regions are adjacent to each other and each have a width of one detecting element in their adjacent directions, and
wherein the radiation absorber has a width of 50% to 150% of the width of the one detecting element in the adjacent directions.

15. The radiation detecting apparatus according to claim 11, wherein a position of a center of the radiation absorber in a direction of proximity of the first and second detecting element regions to each other is an intermediate position between the first and second detecting element regions.

16. The radiation detecting apparatus according to claim 11, wherein the first absorption part and second absorption part have widths in a slice (SL) direction.

17. The radiation detecting apparatus according to claim 11, wherein the first absorption part and second absorption part are integrally formed.

18. A radiation tomographic imaging apparatus comprising:
a radiation source;
a radiation detector including a plurality of detecting elements arranged in channel and slice directions;
a single radiation absorber with a plurality of absorption parts; wherein a first absorption part covers first element parts of first and second detecting element regions in the radiation detector, said first element parts lying on mutually adjoining sides of the first and second detecting element regions; and wherein a second absorption part covers second element parts of third and fourth detecting element regions in the radiation detector, said second element parts lying on mutually adjoining sides of the third and fourth detecting element regions and
a specifying device configured to specify, based on intensities of radiation emitted from a focal point of the radiation source and detected by the detecting elements in the first, second, third, and fourth detecting element regions, a position of the focal point of the radiation source or an amount of movement thereof from a reference position.

19. The radiation tomographic imaging apparatus according to claim 18, wherein a width of the radiation absorber in a direction of proximity of the first and second detecting element regions to each other is wider than a thickness of each of a plurality of collimator plates configured to separate the detecting elements.

20. The radiation tomographic imaging apparatus according to claim 18, wherein the first and second detecting element regions are adjacent to each other in the slice direction.

21. The radiation tomographic imaging apparatus according to claim 18, wherein the first and second detecting element regions are adjacent to each other and each have a width of one detecting element in their adjacent directions, and wherein the radiation absorber has a width of 50% to 150% of the width of the one detecting element in the adjacent directions.

22. The radiation tomographic imaging apparatus according to claim 18, wherein a position of a center of the radiation absorber in a direction of proximity of the first and second detecting element regions to each other is an intermediate position between the first and second detecting element regions.

* * * * *